(12) United States Patent
Sinha et al.

(10) Patent No.: US 6,566,557 B2
(45) Date of Patent: May 20, 2003

(54) PROCESS FOR THE PREPARATION OF SUBSTITUTED TRANS-CINNAMALDEHYDE, A NATURAL YELLOW DYE, FROM PHENYLPROPANE DERIVATIVES

(75) Inventors: Arun Kumar Sinha, Himachal Pradesh (IN); Bhupendra Prasad Joshi, Himachal Pradesh (IN); Ruchi Dogra, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 43 days.

(21) Appl. No.: 09/805,832

(22) Filed: Mar. 14, 2001

(65) Prior Publication Data

US 2002/0133045 A1 Sep. 19, 2002

(51) Int. Cl.$^7$ .......................... C07C 45/28; C07C 45/36
(52) U.S. Cl. ....................................... 568/431
(58) Field of Search ......................................... 568/431

(56) References Cited

U.S. PATENT DOCUMENTS

| 4,532,365 A | 7/1985 | Khoobiar .................... 568/479 |
| 5,811,588 A | 9/1998 | Castelijns et al. .......... 568/434 |
| 5,939,581 A | 8/1999 | Muller et al. ............... 562/410 |

OTHER PUBLICATIONS

Lutz et al., "The Mechanism of Oxidation of Arylpropenes to Arylpropenals", Tetrahedron Letters, No. 55, 1970, pp. 4851–4854.
Zakharkin et al., "The Preparation of Aldehydes by Reduction of Dimethylamides of Carboxylic Acids with Sodium Aluminhohydride", Tetrahedron Letters, vol. 25, 1969, pp. 5555–5559.
Jeong et al., "Cinnamaldehydes Inhibit Cyclin Dependent Kinase 4/Cyclin D1", Bioorganic & Medicinal Chemistry Letters, vol. 10, 2000, pp. 1819–1822.
Kikuzaki et al., "Phenylbutanoid dimers from the leaves of Alpinia flabellata", Phytochemistry, vol. 56, 2001, pp. 109–114.
Kikuzaki et al., "Antioxidative phenylpropanoids from berries of Pimenta dioica", Phytochemistry, vol. 52, 1999, pp. 1307–1312.
Kim et al., "In Vitro Inducible Nitric Oxide Synthesis Inhibitory Active Constituents from Fraxinus rhynchophylla", Planta Medica, vol. 65, 1999, pp. 656–658.
Lee et al., "Inhibition of Human Tumor Growth by 2'–Hydroxy– and 2'–Benzoyl–Oxycinnamaldehydes", Planta Medica, vol. 65, 1999, pp. 263–266.
Oprean et al., "Essential oils analysis. I. Evaluation of essential oils composition using both GC and MS fingerprints", Journal of Pharmaceutical & Biomedical Analysis vol. 18, 1998, pp. 651–657.
Oprean et al., "Comparison of GC–MS and TLC techniques for asarone isomers determination", Journal of Pharmaceutical and Biomedical Analysis, vol. 18, 1998, pp. 227–234.
Iersel et al., Abstract of "Interactions of α,β–unsaturated aldehydes and ketones with human gluththione S–P1–1", Chemico–Biological Interactions, vol. 108, Issue 1–2, Dec. 1997, 2 pgs.
Clark et al., Abstract of "Human food flavor additives as bird repellents: I. Conjugated aromatic compounds", Pesticide Science, vol. 55, Issue 9, 1999, 2 pgs.
Koh et al., Abstract of "Cinnamaldehyde inhibits lymphocyte proliferation and modulates T–cell differentiation", International Journal of Immunopharmacology, vol. 20, Issue 11, 1998, 2 pgs.
J. Geier, Abstract of "Epicutaneous reactions to cinnamic alcohol and cinnamic aldehyde", Dewrmatosen in Beruf and Umwelt, vol. 45, Issue 1, 1997, 2 pgs.
Lu et al., Abstract of "Highly Selective Syntheses of Coniferyl and Sinapyl Alcohols", J. Agric. Food Chem., vol. 46, Issue 5, 1998, 1 pg.
Kwon et al., "Synthesis and Biological Activity of Cinnamaldehydes as Angiogenesis Inhibitors", Biorganic & Medicinal Chemistry Letters, vol., 7, No. 19, 1997, pp. 2473–2476.
Sakamoto et al., "The Palladium–Catalyzed Arylation of 4H–1,3–Dioxin", Tetrahedron Letters, vol. 33, No. 45, 1992, pp. 6845–6848.
Barik et al., "Two Phenolic Constituents from *Alpinia Galanga* Rhizomes", Phytochemistry, vol. 26, No. 7, pp. 2126–2127 (1986).
Ramegowda et al., A New Synthesis of Aldehydes from Acids via Reduction of N–Acyl Saccharins Using Sodium Dihydro Bis–(2–Methoxy–Ethoxy) Aluminate, Tetrahedron, vol. 29, 1973, pp. 3985–3986.
Saxena, "Phenyl Indane from *Acorus Calamus*", Phytochemistry, vol. 25, No. 2, 1986, pp. 553–555.

Primary Examiner—Samuel Barts
Assistant Examiner—Sikarl A. Witherspoon
(74) Attorney, Agent, or Firm—RatnerPrestia

(57) ABSTRACT

The present invention relates to the preparation of substituted trans-cinnamaldehyde, a natural yellow dye from Phenylpropane derivatives having $R_2$—$R_3$—$R_4$—$R_5$—$R_6$ substitution, wherein $R_2$ to $R_6$ equal or different, being hydrogen or hydroxy or acyl or halogen or alkyl or heterocyclic or aryl or dioxymethylene or alkoxy groups, etc., by oxidizing the said phenylpropane derivatives using a oxidising agent such as 2,3-dichloro-5,6-dicyano-1,4-benzoquinone (DDQ) or p-chloranil or pyridinium chlorochromate (PCC) or tBuOOH or $CrO_3$ with a catalytic amount of inorganic/organic acid or alumina, celite, and silica gel as a solid support for microwave irradiation and thus substituted trans-cinnamaldehydes, a natural yellow dye, are obtained in high yield ranging from 68–82%.

23 Claims, 4 Drawing Sheets

$^1$H NMR (300 MHz) spectra of 2,4,5-trimethoxycinnamaldehyde in CDCl$_3$

Mass spectra of 2,4,5-trimethoxycinnamaldehyde (MW 222)

Formula I

PROCESS FOR THE PREPARATION OF SUBSTITUTED TRANS-CINNAMALDEHYDE, A NATURAL YELLOW DYE, FROM PHENYLPROPANE DERIVATIVES

FIELD OF THE INVENTION

The present invention relates to "A process for the preparation of substituted trans-cinnamaldehyde, a natural yellow dye, from phenylpropane derivatives" in which trans-cinnamaldehyde (e.g. 2,4,5-trimethoxycinnamaldehyde where $R_1$ is —CH=CH—CHO, $R_2=R_4=R_5$ is —OMe and $R_3=R_6$ is H; p-methoxycinnamaldehyde where $R_1$ is —CH=CH—CHO, $R_2=R_3=R_5=R_6$ is H, $R_4$ is —OMe and 3,4-dimethoxycinnamaldehyde where $R_1$ is —CH=CH—CHO, $R_2=R_5=R_6$ is H and $R_3=R_4$ is —OMe etc) of the formula I as shown below:

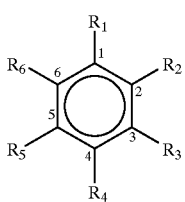

Formula I

These compounds can be obtained by oxidation of ($R_2$—$R_3$—$R_4$—$R_5$—$R_6$)phenylpropane derivatives (wherein $R_2$ to $R_6$ equal or different, being hydrogen or hydroxy or alkyl or methylenedioxy or alkoxy groups, etc) which is, in fact, a reduced product of readily available natural phenylpropene (methyl chavicol, anethole, eugenol, methyl isoeugenol, safrole, toxic β-asarone etc) bearing essential oil or the like.

BACKGROUND OF THE INVENTION

Cinnamaldehyde and its substituted derivatives (e.g. p-methoxy cinnamaldehyde, 3,4-methylenedioxycinnamic aldehyde, coniferyl aldehyde etc) possess an aromatic ring bearing one or more hydroxy or dioxymethylene or alkoxy groups or the like, attached to the α,β-unsaturated aldehyde (i.e. CH=CH—CHO) which contribute significantly to the taste and flavour of many foods and drinks (Harbome, J. B. and Baxter, H., In: Phytochemical Dictionary, A Handbook of Bioactive Compounds from Plants, Taylor & Francis Ltd., London WC1N 2ET, 472–488 (1993)). In addition, cinnamaldehyde derivatives serve as a raw material for the preparation of a number of other perfumery aromatics. Morever, the selective reduction of the aldehyde group gives cinnamyl alcohol which possesses a pleasant and long-lasting spicy odor and complete reduction of the side chain gives phenyl propyl alcohol and its oxidation give hydrocinnamic acid (Muller, A. J., Bowers Jr, J. S., Eubanks, J. R., Geiger, C. C. and Santobianco, J. G., U.S. Pat. No. 5,939, 581)) which, along with its ester, finds usage in perfumery composition. Cinnamaldehyde and its derivatives are not only found to be highly effective to prevent skin from darkening caused by irradiation of ultraviolet rays from the sun (Tomoshi, K. and Makoto, F., JP Pat. No. 58055414A2)) but also proved to be excellent in preventing falling-off of hair and also provide hair growth (Watanabe, T., Komeno, T. and Hatanaka, M., JP Pat. No. 6312916A2)). In addition, cinnamaldehyde in combination with the manure controls injurious microorganisms present in soil without any adverse effect on manure-decomposing microorganisms (Saotome, K., JP Pat. No. 58201703A2)). Further, cinnamaldehyde derivatives are useful as an intermediate for synthesis of various drugs such as anti-viral pharmaceuticals, particularly HIV protease inhibitors (Castelijns, A. M. C. F., Hogeweg, J. M. and van Nispen, S. P. J. M., U.S. Pat. No. 5,811,588) and also used in cosmetics, dyes, agrochemicals, alkaloids (Parmar, V. S., Jain, S. C., Bisht, K. S., Jain, R., Taneja, P., Jha, A., Tyagi, O. D., Prasad, A. K., Wengel, J., Olsen, C. E. and Boll, P. M., Phytochemistry, 46(4): 597–673 (1997)), perfumes, etc.

Cinnamaldehyde is identified for the first time in the year 1833 during steam distillation of Ceylon bark of cinnamon (*Cinnamomum zeylanicum*, family: Lauraceae) which is still one of the main source of cinnamaldehyde. It also occurs in dozens of flowers and essential oils such as Hyacinthus spp., Narcissus spp., Lavandula spp., *Pogostemon cabline* and Commiphora spp. and others. However, substituted cinnamaldehyde (coniferyl aldehyde or coniferaldehyde or ferula aldehyde or ferulaldehyde) occurs in a number of other plants such as Quercus spp., *Acer saccharinum* which, imparts a phenolic-spicy, sweet balsamic odour and is used extensively in flavour compositions. Similarly, sinapaldehyde (3,5-dimethoxy-4-hydroxycinnamaldehyde) occurs in *Juglans nigra, Senra incana* and p-methoxycinnamaldehyde in *Acorus gramineu* etc. Mostly, substituted cinnamaldehydes are yellow in color; therefore, the applicability of cinnamaldehyde can be further increased with the possibities of their uses in the area of natural dyes. However, the limited percentage of substituted cinnamaldehydes present in the plant kingdom is not sufficient to fulfill the world demand. As a result, the major amounts of cinnamaldehydes are made synthetically.

A number of proceses have been proposed to produce cinnamaldehyde and its derivatives (such as p-methoxycinnamaldehyde, dimethoxycinnamaldehyde, sinapaldehyde, trimethoxycinnamaldehyde and methylenedioxy cinnamaldehyde etc). For the most part, these methods involve reaction of the substituted benzaldehyde (such as p-methoxybenzaldehyde etc) with acetaldehyde in the presence of acid or better with alkali. Cinnamaldehyde can also be prepared by hydrolysis of cinnamylidene chloride. Good yields have been obtained by the Rosenmund reduction of cinnamic acid chloride with palladinium catalyst (March, J., In: Advanced Organic Chemistry, Reactions, Mechanisms and Structure, Wiley Eastern Ltd., New Delhi, 396–397, (1987)). Catalytic dehydrogenation of cinnamic alcohol at high temperature under reduced pressure has given good yields of cinnamaldehyde. Dry distillation of the calcium salts of cinnamic and formic acid also yields aldehyde. Isomerization of phenylethynyl carbinol in the presence of acid produces good yields of aldehyde. A practical method of producing a range of α,β-unsaturated aldehyde is to treat an olefin with carbon monoxide under pressure and in the presence of a catalyst (Brown, H. C. and Tsukamoto, A., J. Am. Chem. Soc., 86: 1089 (1964)) and Bedoukian, P. Z., In: Perfumery and Flavoring Synthetics, Allured Publishing Corporation, Wheaton, Ill., USA, 98–105 (1986)). Though such methods have been proven to be useful, they suffer from one or more process deficiencies. For example, in some instances processes of this type necessarily involve resort to sub-ambient temperatures, which of course, involves some considerable process control and in some cases, the reaction is effected only at a relatively high pressures and lead to reaction mixtures.

Typical prior art references include U.S. Pat Nos. 2,529, 186; 2,794,813; 3,028,419 and German Patent Nos. 97,620; 1,114,798 and Soviet Union Pat. No. 1451139A1 and Czechoslovakia Pat. No. 8405411A1.

It, therefore, becomes an object of invention to provide a process for producing cinnamaldehydes such as p-methoxycinnamaldehyde, 3,4-dimethoxycinnamaldehyde, 3,4-methylenedioxycinnamaldehyde, 3,4-methylenedioxy-5-methoxycinnamaldehyde, 1-ethoxy-2-acetoxycinnamaldehyde, 1-ethoxy-2-hydroxycinnamaldehyde, sinapaldehyde, 2,5-dimethoxy-3,4-methylenedioxycinnamaldehyde, 2-methoxy-4,5-methylenedioxy cinnamaldehyde, coniferyl aldehyde, 3,4,5-trimethoxycinnamaldehyde, 2,3-dimethoxy-4,5-methylenedioxycinnamaldehyde and 2,4,5-trimethoxycinnamaldehyde or the like, by means which eliminate the above discussed disadvantages and others.

Other objectives will appear hereinafter.

OBJECTIVES OF THE INVENTION

The main object of the present invention is to develop a simple industrial process for the preparation of substituted cinnamaldehyde (such as p-methoxycinnamaldehyde, 3,4-dimethoxycinnamaldehyde, 2,4,5-trimethoxycinnamaldehyde etc) in one step with high yield from phenylpropane derivatives (such as dihydro methylchavicol, dihydro methyleugenol, 2,4,5-trimethoxyphenylpropane etc) which is, in fact, the hydrogenated product of readily available natural phenylpropenes (such as, methyl chavicol or anethole, methyl eugenol, highly toxic β-asarone etc.)

In another object of the invention is to develop a simple process for the preparation of substituted cinnamaldehyde in high purity without any contamination of corresponding cinnamicacid and alcohol.

Yet another object of the present invention is to develop a process for the preparation of trans-cinnamaldehyde exclusively in a single step from phenylpropane derivatives.

Yet another object of the invention is to develop a simple process for the preparation of substituted cinnamaldehyde, a natural yellow dye, on commercial scale for multifarious applications such as for colouring and flavouring foods and also for pharmaceutical industries etc.

Yet another object of the invention is to develop a simple and quick process for the preparation of substituted cinnamaldehyde in a short time ranging from a few seconds to a few minutes under microwave irradiation.

Yet another object of the invention is to develop a process for the preparation of substituted cinnamaldehyde utilizing simple and cheaper dihydroproduct obtained from readily available natural phenylpropene bearing oil such as methyl chavicol, anethole, eugenol etc.

Yet another object of the invention is to prepare substituted cinnamaldehyde utilizing otherwise toxic essential oil e.g. safrole or β-asarone or the other like toxic oil thereby, enhancing the profitable use thereof.

Yet another object of the invention is to provide a process for the preparation of 2,4,5-trimethoxycinnamaldehyde or the like for the first time which is useful as a simple starting material for synthesis of corresponding cinnamic acid, esters, amide derivatives and other uses thereof for synthesis of heterocyclic and biologically active compounds.

SUMMARY OF THE INVENTION

Accordingly, the present invention provides a process for the preparation of substituted trans-cinnamaldehyde from phenylpropane derivatives utilizing 2,3-dichloro-5,6-dicyano-1,4-benzoquinone (DDQ) as an efficient oxidizing agent in the presence of catalyst namely acetic acid, p-toluenesulphonic acid, silica gel.

DETAILED DESCRIPTION OF THE INVENTION

Accordingly the present invention provides, a process for the preparation of substituted trans cinnamaldehyde, a natural yellow dye, of Formula 1 ##STR## as shown in FIG. 4 of the accompanying drawing wherein, $R_1$ is fixed as a —CH═CH—CHO, however, $R_2$, $R_3$, $R_4$, $R_5$, $R_6$ are independently selected from i) a hydrogen atoms ii) a alkoxy group but atleast two of them from $R_2$, $R_3$, $R_4$, $R_5$, $R_6$ are hydrogen atom or a alkoxy group but one methylenedioxy group with combination of either hydroxyl group, alkoxy group, alkyl group having 1–2 carbon atoms, aryl group or hydrogen atom or a alkoxy group but one hydroxyl group with combination of either methylenedioxy group, hydroxyl group, alkoxy group, alkyl group having 1–2 carbon atoms, aryl group or hydrogen atom; iii) a methylenedioxy with atleast three of them $R_2$, $R_3$, $R_4$, $R_5$, $R_6$ are combination of either alkoxy, hydroxy group, alkyl group having 1–2 carbon atoms, aryl group or hydrogen atom; vi) a hydroxyl group but atleast one of them from $R_2$, $R_3$, $R_4$, $R_5$, $R_6$ is hydrogen atom with combination of either alkoxy, hydroxyl group, methylenedioxy group, alkyl group having 1–2 carbon atoms, aryl group or hydrogen atom; vii) a protected hydroxyl group such as acetyl, benzyl, but atleast one of them from $R_2$, $R_3$, $R_4$, $R_5$, $R_6$ is hydrogen atom with combination of either alkoxy, hydroxyl group, methylenedioxy group, alkyl group having 1–2 carbon atoms, aryl group or hydrogen atom, obtained from corresponding ($R_2$—$R_3$—$R_4$—$R_5$—$R_6$)phenylpropane derivatives, said process comprising oxidizing substituted phenylpropane derivatives in presence of a solvent and a catalyst using an oxidizing agent in a mole ratio of 1:1 to 1:8 to the phenyl propane derivatives at a temperature between −15 to +210° C. for a period of 30 minutes to 48 hours, removing the solvent under reduced pressure and isolating the product in a conventional manner to obtain a yield between 68–82% of trans cinnamaldehyde of formula 1.

It is worthwhile to mention that the above cost effective process is an accidental result of two individual steps (i.e. dehydrogenation and oxidation) observed for the first time during DDQ assisted oxidation of phenylpropane which is, in fact, the reduced product of readily available natural phenylpropenes (such as methyl chavicol, eugenol, dimethylisoeugenol etc.) including some toxic and an internationally banned isomer of phenylpropene derivatives such as safrole and -asarone.

In one embodiment of the invention, the solvent used is selected from the group consisting of diethyl ether, tetrahydrofuran, dimethoxyethane, dioxane, diphenylether, chlorinated solvent selected from such as dichloromethane, chloroform and o-dichlobenzene, an aromatic hydrocarbon selected from benzene, toluene, xylene and organic acid selected from formic acid, acetic acid.

In another embodiment of the invention, the oxidizing agent used is selected from the group consisting of 2,3-dichloro-5,6-dicyano-1,4-benzoquinone (DDQ), p-chloranil, pyridinium chlorochromate (PCC), tBuOOH, $CrO_3$ and a mixtures thereof.

In still another embodiment of the invention, the mole ratio of oxidizing agent to reactant is ranging from 1:1.5 to 1:5.

In yet another embodiment of the present invention, the reaction temperature is ranging from 30° C. to 140° C.

In yet another embodiment of the present invention, reaction period is ranging 4–16 hours.

In yet another embodiment of the present invention, the catalyst used is selected from a group comprising hydrochloric acid, sulfuric acid, Cu(I) or Fe(III) salt, periodic acid, organic acid selected from acetic acid, propionic acid, butyric acid, ion exchange resin selected from IR-120H and a sulphonated polystyrene resin, para-toluenesulphonic acid (PTSA) and amberlyst such as amberlyst 15.

In yet another embodiment of the present invention, the starting material phenylpropane used is obtained by reduction of allylbenzene or phenyl propene derivatives or widely available natural allyl/phenyl propene derivatives exiting in all three isomeric forms.

In yet another embodiment of the present invention, the oxidation of phenylpropane provides trans-cinnamaldehyde, which is similar to the isomer produced by plants.

In yet another embodiment of the present invention, toxic beta (cis) and γ-isomer are converted into value added natural dyes.

In yet another embodiment of the present invention, an internationally banned beta-asarone from Acorus calamus is utilized by its conversion into a useful natural yellow dye.

In yet another embodiment of the present invention, the process is capable of preparing cinnamaldehyde derivatives on commercial scale.

In yet another embodiment of the present invention, the above process is capable of providing some new kind of cinnamaldehyde derivatives, which are useful as natural colorants, antioxidant and antimicrobial agents.

In yet another embodiment of the present invention, the above process provides $DDQH_2$ (by product) 91–94% and its regeneration into DDQ also reduces the cost of production of cinnamaldehyde derivatives.

In yet another embodiment of the present invention, the above process is capable to oxidize phenyl alkane having 2n−1 carbon atoms wherein, n varies from 2 to 6 or more into corresponding unsaturated aldehydes.

In yet another embodiment of the present invention, the above phenylpropane derivatives are capable of undergoing various kind of reactions such as halogenation, dehydrogenation, allylic halogenation, formulation, mono and/or dicarbonylation, condensation.

In yet another embodiment of the present invention, the above process provides cinnamaldehyde derivatives without any contamination of corresponding acid and alcohol.

In yet another embodiment of the present invention, in above process some of cinnamaldehyde such as 2,4,5-trimethoxycinnamaldehyde is obtained in good yield, which finds application as a simple starting material for the synthesis of corresponding various new unsaturated acids, esters, amides, alcohol derivatives.

In yet another embodiment of the present invention, some of cinnamaldehyde such as 2,4,5-trimethoxycinnamaldehyde is obtained in good yield which finds application as a simple starting material for the synthesis of corresponding various new dihydro (saturated) acids, esters, amides and alcohols derivatives.

In yet another embodiment of the present invention, the products obtained are (i) 2,4,5-trimethoxycinnamaldehyde where $R_1$ is —CH=CH—CHO, $R_2=R_4=R_5$ is —OMe and $R_3=R_6$ is H, (ii) p-methoxycinnamaldehyde where $R_1$ is —CH=CH—CHO, $R_2=R_3=R_5=R_6$ is H and $R_4$ is —OMe and (iii) 3,4-dimethoxycinnamaldehyde where $R_1$ is —CH=CH—CHO, $R_2=R_5=R_6=$H and $R_3=R_4$ is —OMe.

In one more embodiment the present invention provides a process for the preparation of substituted trans-cinnamaldehyde, a natural yellow dye, of Formula 1, said process comprising oxidizing substituted phenylpropane derivatives in presence of a solvent and a catalyst using an oxidizing agent in a mole ratio of 1 to 20 with a solid support under micro wave radiation at a medium power 600 W for a period ranging from 20 seconds to 12 minutes, removing the solvent under reduced pressure and isolating the product in a conventional manner to obtain the trans-cinnamaldehyde of formula 1.

In yet another embodiment of the present invention, the solid support used is selected from a group comprising celite, silica gel, molecular sieve and alumina.

In yet another embodiment of the present invention, the products obtained through the microwave radiation process are (i) 2,4,5-trimethoxycinnamaldehyde where $R_1$ is —CH=CH—CHO, $R_2=R_4=R_5$ is —OMe and $R_3=R_6$ is H, (ii) p-methoxycinnamaldehyde where $R_1$ is —CH=CH—CHO, $R_2=R_3=R_5=R_6$ is H and $R_4$ is —OMe and (iii) 3,4-dimethoxycinnamaldehyde where $R_1$ is —CH=CH—CHO, $R_2=R_5=R_6$ is H and $R_3=R_4$ is —OMe.

In short, the present invention provides a process for the preparation of substituted trans-cinnamaldehyde, a natural yellow dye, from phenylpropane derivatives wherein R.sup.1 is fixed as a —CH=CH—CHO, however, R.sup.2, R.sup.3, R.sup.4, R.sup.5, R.sup.6 are independently; i) a hydrogen atoms ii) a alkoxy group but atleast two of them from R.sup.2, R.sup.3, R.sup.4, R.sup.5, R.sup.6 are hydrogen atom or a alkoxy group but one methylenedioxy group with combination of either hydroxyl group, alkoxy group, alkyl group having 1–2 carbon atoms, aryl group or hydrogen atom or a alkoxy group but one hydroxyl group with combination of either methylenedioxy group, hydroxyl group, alkoxy group, alkyl group having 1–2 carbon atoms, aryl group or hydrogen atom; iii) a methylenedioxy with atleast three of them from R.sup.2, R.sup.3, R.sup.4, R.sup.5, R.sup.6 are combination of either alkoxy, hydroxy group, alkyl group having 1–2 carbon atoms, aryl group and hydrogen atom; iv) a hydroxyl group but atleast one of them from R.sup.2, R.sup.3, R.sup.4, R.sup.5, R.sup.6 is hydrogen atom with combination of either alkoxy, hydroxyl group, methylenedioxy group, alkyl group having 1–2 carbon atoms, aryl group or hydrogen atom; v) a protected hydroxyl group such as acetyl, benzyl, etc but atleast one of them from R.sup.2, R.sup.3, R.sup.4, R.sup.5, R.sup.6 is hydrogen atom with combination of either alkoxy, hydroxyl group, methylenedioxy group, alkyl group having 1–2 carbon atoms, aryl group and hydrogen atom or the like, obtained from corresponding ($R_2$—$R_3$—$R_4$—$R_5$—$R_6$) phenylpropane derivatives (e.g. dihydro anethole where $R_2=R_3=R_5=R_6$ is H; $R_4$ is —OMe; dihydro methyl eugenol where $R_2=R_5=R_6$ is H; $R_3=R_4$ is —OMe and dihydro asarone where $R_2=R_4=_{R5}$ is —OMe; $R_3=R_6$ is H etc) and the above process comprising the steps of (a) providing phenylpropane such as but not limited to 2,4,5-trimethoxyphenylpropane (dihydroasarone) in the following solvents namely ether such as but not limited to diethyl ether, tetrahydrofuran, dimethoxyethane, dioxane, diphenylether and the like; chlorinated solvents such as but not limited to dichloromethane, chloroform, o-dichlobenzene; an aromatic hydrocarbon such as but not limited to benzene, toluene, xylene; organic acid such as but not limited to formic acid, acetic acid and the like; (b) oxidation of phenylpropane derivatives in the presence of oxidizing reagents such as but not the limited to 2,3-dichloro-5,6-dicyano-1,4-benzoquinone (DDQ) or p-chloranil or pyridinium chlorochromate (PCC) or tBuOOH or $CrO_3$ or a combination of reagents and the like and the amount thereof to be used is in the ration of 1–20 times moles, preferably 1.5–8 times moles, reaction temperature varies from −15° C. to +210° C., preferably 30° C. to 140° C., reaction period varies from 30 minutes to 48 hours, preferably 4–16 hours; (c) oxidation step proceeds more smoothly along with higher yield in presence of catalysts mainly mineral acid such as but not limited to hydrochloric acid, sulphuric acid or Cu(I) or Fe(III) salt or periodic acid or organic acid such as but not limited to acetic acid, propionic acid, butyric acid, ion exchange resin such as IR-120H, a sulphonated polystyrene resin, para-toluenesulphonic acid (PTSA) or amberlyst such as amberlyst 15 or absorbed above solution of phenylpropane and oxidising reagent on the following solid support such as but not limited to celite, silica gel, molecular sieve, alumina and the like in a short period ranging from 20 seconds to 12 minutes under microwave irradiation; (d) filtering the mixture and removing the solvent under reduced pressure, where the product is to be isolated in a conventional manner, i.e. extraction, distillation, recrystallization and chromatography and the yield of the product (e.g. 2,4,5-trimethoxycinnamaldehyde where $R_1$ is —CH═CH—CHO, $R_2$═$R_4$═$R_5$ is —OMe; $R_3$═$R_6$ is H; and 3,4-dimethoxycinnamaldehyde where $R_1$ is —CH═CH—CHO, $R_2$═$R_5$═$R_6$═H; $R_3$═$R_4$ is —OMe etc. in the above formula I) varies from 68–82%, preferably more in case of benzoquinone as a oxidising reagent.

In an embodiment of the present invention, a simple process is described in order to obtain substituted trans-cinnamaldehyde. In fact, a simple and cheaper starting material phenylpropane derivatives obtained from hydrogenation of widely available natural phenylpropene is utilized for high valued cinnamaldehyde derivatives.

In another embodiment of the present invention, a simple and one step process is described for substituted cinnmaldehydes in high puLrity and yield without contamination of corresponding acid and alcohol.

In another embodiment of the present invention, substituted cinnamaldehydes are used as a natural yellow dye for colouring food, textile and pharmaceutical products etc.

In another embodiment of the present invention is a simple process, available for commercial scale production.

Phenylpropanoids (C6–C3) comprises of the compounds in which derivatives of phenylpropene, phenylpropanone, cinnamaldehyde, cinnamal alcohol, cinnamic acid and ester are found to be biologically active and have commercial importance. Among these phenylpropanoids, the ($R_2$—$R_3$—$R_4$—$R_5$—$R_6$) cinnamaldehyde derivatives wherein $R_2$ to $R_6$ equal or different, being hydrogen or hydroxy or methylenedioxy or alkoxy groups, etc are frequently present in the essential oil. As per applications concern, these cinnamaldehydes are widely used in fragrance, flavour, cosmetic, liquor and in pharmaceuticals, etc and are also utilized as pheromones, antibacterial, antifungal etc in the insect world. The wide use of cinnamaldehydes (F.E.M.A. no. 2286) ranging from flavouring agents to pharmaceuticals and their importance as an intermediate in the synthesis of biologically active compounds have always attracted attention of chemists (Muller, A. J., Bowers Jr, J. S., Eubanks, J. R., Geiger, C. C. and Santobianco, J. G., U.S. Pat. No. 5,939, 581 and Castelijns, A. M. C. F., Hogeweg, J. M. and van Nispen, S. P. J. M., U.S. Pat. No. 5,811,588)). The principal source of cinnamaldehyde (synonyms: cinnamic aldehyde or 3-phenylpropenal or cinnamal or gamma-phenylacrolein or cassia aldehyde) is the bark of cinnamon (*Cinnamomum zeylanicum*; Lauraceae) and its fresh bark contains high levels of cinnamyl acetate which releases cinnamaldehyde by fermentation processes applied during commercial preparation by enzymatic hydrolysis and participation of the reversible aldehyde-alcohol oxidoreductase. Cinnamon leaf, on the other hand, contains large amounts of eugenol and much smaller amounts of cinnamaldehyde. Similarly, another source of cinnamaldehyde is *Cinnamornum cassia* which is widely used in traditional Chinese medicine (Tang, W. and Eisenbrand, G. In: Chinese Drugs of Plant Origin, Springer-Verlag, New York, pp. 319–330 (1992)) as an analgesic, stomachic and anti-inflammatory agent and its activity is found due to high percentage of cinnamaldehyde (85%). In addition, cinnamaldehyde has shown anti-mutagenic activity towards chemical mutagens or UV irradiation (Kakimuma, K., Koike, J., Kotanik, K., Ikekawa, W., Kado, T. and Nomoto, M., Agric. Biol. Chem. 48: 1905–1906 (1984); Ohta, T., Watanabe, K., Moriya, M., Shirasu, Y., Kada, T., Mutat. Res., 107: 219–227 (1983)). Cinnamaldehyde at a concentration of 4.8 μg/ml inhibited the growth of L 1210 leukemia cells in culture by 50% and its aldehydydic group is found to be responsible for the above inhibition. Cinnmaldehyde also inhibited the growth of SV40-induced tumor W2K-11 in mice (CA 94: 168054k and Moon, K. H., Pack, M. Y., Drug Chem., Toxicol, 6: 521–535 (1983)).

Similarly, a number of substituted cinnamaldehydes such as ortho-methoxy cinnamaldehyde (synonym: ortho-cumeric aldehyde methyl ether), para-methoxy cinnamaldehyde (synonym: para-cumeric aldehyde methyl ether), 3,4-dimethoxy cinnamic aldehyde (synonyms: homoconiferaldehyde or methyl ferulaldehyde), para-coniferaldehyde (synonyms: ferulaldehyde or maple aldehyde or 4-hydroxy-3-methoxy cinnamic aldehyde), 3,4-methylenedioxycinnamic aldehyde (synonyms: piperonyl acrolein or heliotropylidene acetaldehyde or piperonylidene acetaldehyde), sinapaldehyde (synonym: 2,4-dimethoxy-4-hydroxy cinnamic aldehyde) are also widely used in flavour compositions, however, the odour of these substituted cinnamaldehydes bears a little organoleptic resemblance to that of cinnamaldehyde. In addition, some substituted cinnamaldehydes are known for their biological activities. 2'-hydroxycinnamaldehyde inhibits farnesyl-protein transferase (FPTase) (Knon, B. M.; Cho, Y. K., Lee, S. H., Nam, J. Y., Bok, S. H., Chun, S. K., Kim, J. A. and Lee, I. R., Planta Medica, 62: 183–184 (1996)) and also acts as active anticancer compound (Lee, C. W., Hong, D. H., Han, S. B., Park, S. H., Kim, H. K., Kwon, B. M. and Kim, H. M., Planta Medica, 65: 263–266 (1999)). 3',4'-dimethoxycinnamaldehyde reduces the contractile response of guinea pig ileal strips to $LTD_4$. Similarly, substituted cinnamaldehyde such as 4-hydroxy-3-methoxycinnamaldehyde is a potent antioxidant compound (Kikuzaki, H., Hara, S., Kawai, Y. and Nakatani, N., Phytochemistry, 52, 1307–1312 (1999)) and also found as an inducible nitric oxide synthesis (iNOS) inhibitory compound (Kim, N. Y., Pae, H. O., Ko, Y. S., Yoo, J. C., Choi, B. M., Jun; C. D., Chung, H. T., Inagaki, M., Higuchi, R. and Kim, Y. C., Planta, Medica, 65, 656–658 (1999)). However, substituted cinnamic aldehyde are found in traces in plants kingdom and alternatively, they can be obtained by chemical synthesis. Some of the important methods are:

(a) reaction of substituted benzene derivative with nitroso dimethylaniline in the presence of mineral acid and catalyst (CA 51, 7326 (1957);

(b) condensation of vinyl ether with arylaldehyde acetal (Friedrich and Hartmann, Chem. Ber., 94, 838 (1961);

(c) reaction of Grignard of bromobenzene with 1-(N-Methylanilino)propen-3-al (Jutz, Ger. Pat. 1,114,798, Oct. 12, (1961);

(d) reaction of appropriate olefin with carbon monoxide under pressure and in the presence of catalysts (U.S. Pat. No. 3,028,419, Apr. 3, (1962));

(e) claisen-Schmidt reaction of arylaldehyde with acetaldehyde offers cinnamaldehyde in the range of 12 to 30% depending upon the arylaldehyde used. The low yield of this reaction product is, perhaps, due to self-condensation of acetaldehyde (Richmond, U.S. Pat. No. 2,529,186, Nov. 7, (1950);

(f) reaction of arylaldehyde with triethyl phosphonoacetate followed by reduction of ethyl cinnamate with lithium aluminium hydride (LAH) to corresponding cinnamyl alcohol and then oxidation of cinnamyl alcohol with $MnO_2$ into cinnamaldehyde (Rajasekhar, D. and Subbaraju, G. V. Indian. J. Chem. 38, 837–838 (1999)). However, this is a multistep process and requires expensive reagents;

(g) reaction of cinnamic acid with thionyl chloride followed by reduction with bis(triphenylphosphine) tetrahydroborate copper (El-Feraly, F. S. and Hoffstetter, M. D. J. Nat. Prod. 43, 407 (1980);

(h) reaction of arylaldehyde with poisonous potassium cyanide reagent (Deuchert, S. K., Hertenstein, U. and Hunig, S., Synthesis, 777 (1973); and (i) reaction of N,N-dimethylbenzamide with lithium diethoxyaluminium hydride (Perun, T. J., Zeftel, L., Nelb, R. G. and Tarbell, D. S., J. Org. Chem., 28, 2937 (1963).

All the above methods have various limitations, for example, low yield, expensive reagents and formation of unwanted side products. It is rather curious that in spite of very large quantities of cinnamaldehyde manufactured annually, the chemical and patent literatures on the subject of its manufacture are quite meager. Keeping in view of all the above problem, we have invented a simple industrial process for preparation of substituted cinnamaldehyde in a single step from phenylpropane. To the best of the applicants knowledge, oxidation of phenylpropane derivatives into substituted cinnamaldehyde derivatives have not been reported earlier. This simple starting material can be obtained by reduction of double bond of phenylpropenes bearing essential oil (such as methyl chavicol, anethole, methyl eugenol, safrole, β-asarone etc). In addition, phenylpropane derivatives can be prepared by Grignard reaction of benzyl chloride derivatives with diethyl sulphate (Organic Synthesis, Coll. Vol 1, pp 471). However, it is worthwhile to mention that the applicants' above process for the preparation of substituted cinnamaldehyde has been invented during the development of a process for the preparation of pharmacological active trans-phenylpropene (α-asarone) (Janusz, P., Bozena, L., Alina, T. D., Barbara, L., Stanislaw, W., Danuta, S., Jacek, P., Roman, K., Jacek, C., Malgorzata, S., Zdzislaw, C., J. Med. Chem., 43, 3671–3676 (2000)) from 2,4,5-trimethoxyphenylpropane, a reduced product of toxic β-asarone.

Phenylpropenes, widely used in fragrance, flavour, cosmetic, liquor, whisky, and pharmaceutical industries, exist in three isomeric form (i.e. α, β and γ), however, cis-isomeric form of phenylpropene (such as β-asarone) has been recently proved to be carcinogenic and toxic (Taylor, J. M., Jones, W. I., Hogan, E. C., Gross, M. A., David, D. A. and Cook, E. L., Toxicol. Appl. Pharmacol., 10: 405 (1967); Keller, K.; Odenthal, K. P. and Leng, P. E., Planta Medica, 1: 6–9 (1985) and Kim, S. C., Liem, A., Stewart, B. C. and Miller, J. A., Carcinogensis, 20(7), 1303–1307 (1999)) and therefore, banned for any kind of use in flavour, perfumery and pharmaceutical industries. Cis-anethol is found to be 15 times more toxic than trans-anethol. Similarly, γ-isomeric form of phenylpropene (such as safrole) is also found carcinogenic (Daimon, H., Sawada, S., Asakura, S. and Sagami, F., Carcinogenesis, 19(1): 141–146, (1998) and Liu, T. Y., Chen, C. C., Chen, C. L. and Chi, C. W., Food & Chemical Toxicology, 37(7): 697–702, (1999). In view of above problem, most affected plant is Acorus calamus (family:Araceae) in which percentage of toxic β-asarone depends upon the varieties of A. calamus (Riaz, M., Shadab, Q., Chaudhary, F. M., Hamdard Medicus 38(2): 50–62 (1995) and McGuffin, M., Hobbs, C., Upton, R. and Goldberg, A., In: American Herbal Products Association's Botanical Safety Handbook, CRC Press, Inc.; Boca Raton, Fla.; USA, 231, (1997)). The content of β-asarone in the triploid variety is 8–19%, while β-asarone reaches upto 96% in the tetraploid and hexaploid varieties (extensively found in Asian countries). In contrast, ‚B-asarone is not found in the diploid variety. As a result, the calamus oil obtained from North American diploid strain (zero, β-asarone) and East European triploid strain (upto 12% β-asarone) are allowed for clinical effectiveness and safety while the calamus oil produced in Asian belt (such as India, Pakistan, Bangladesh, Nepal, Japan and China) has diminished the market potential of calamus oil due to high percentage of β-asarone ranging from 70 to 96% (Mazza, G., J. of Chromatography 328:179–206 (1985); Nigam, M. C., Ateeque, A., Misra, L. N. and Ahmad, A., Indian Perfumer 34: 282–285 (1990) and Bonaccorsi, I., Cortroneo, A., Chowdhury, J. U. and Yusuf, M., Essenze Derv. Agrum, 67(4): 392–402 (1997)). Therefore, the applicants' objective is to utilize toxic β-asarone (cis-2,4,5-trimethoxyphenyl-1-propene) as a simple starting material for value added products via its reduced product (2,4,5-trimethoxyphenylpropane) which has recently been found useful as a new aroma molecule with atleast six to four times less toxic than β-asarone or calamus oil (Sinha, A. K., U.S. Ser. No. 09/652,376 filed Aug. 31, (2000)). Further, 2,4,5-trimethoxyphenylpropane appeared to us as a simple intermediate for the preparation of trans-2,4,5-trimethoxyphenyl-1-propene (α-asarone).

Interestingly, 2,4,5-trimethoxyphenylpropane when treated with 2,3-dichloro-5,6-dicyano-1,4-benzoquinone (DDQ) furnished α-asarone (compared with standard α-asarone) and an intense yellow coloured spot with some unreacted starting material (clearly visible on TLC plate). Increase in the amount of DDQ further favoured the formation of yellow colouring material rather than the α-asarone. All three products were separated on column chromatography in which yellow solid (mp 140° C.) showed IR absorption band at 1648 $cm^{-1}$ (conjugated C=O) and also gave positive 2,4-DNP test, thus, confirming the presence of carbonyl group. UV spectra of yellow solid (λmax 244, 298, 366 nm) confirmed an increase in conjugation than the starting material 2,4,5-trimethoxyphenylpropane (288 nm) and β-asarone (269, 301 nm). $^1$H NMR (FIG. 1) of yellow solid showed the 14 number of protons (see Example I) in which two doublets and one doublet of doublet for three protons appeared at δ 9.65 (1H, d, J=7.8 Hz), 7.81 (1H, d, J=15.8 Hz) and δ 6.64 (1H, dd, J=15.8 Hz, J=7.8 Hz) respectively. Further, the position of two aromatic singlet protons and three singlet for nine protons for three trimethoxy groups were more or less at same δ value as compared to β-asarone (Patra, A. and Mitra, A. K., Phytochemistry, 44: 668–669 (1981)). IR and $^1$H NMR has supported the possibility of unsaturated aldehyde group (—CH=CH—CHO) attached with trimethoxy (nine protons) substituted phenyl ring (two protons). Similarly, the $^{13}$C NMR (FIG. 2) of the yellow solid that appeared at δ 194.1, 154.1, 153.2, 147.6, 143.3, 126.4, 114.5, 110.5, 96.5, 56.4, 56.2, 56.0 clearly indicated the presence of 12 carbons as similar to the 12 carbons of β-asarone except that the position of side propyl group which appeared at δ 194.1 (C-3'), 154.1 (C-1') and 126.4 (C-2') could be possible due to β-unsaturated aldehyde (—CH=CH—CHO) group. The EI mass spectrum (FIG. 3) of yellow solid showed a clear [M]$^+$ peak at m/z 222. On the basis of above spectral data, the yellow solid was postulated to be 2,4,5-trimethoxycinnamaldehyde as a trans-isomer (Example I). The formation of this unexpected trans-2,4,5-trimethoxycinnamaldehyde was finally confirmed by its (i) oxidation with neutral KMnO$_4$ in the cold acetone to well known 2,4,5-trimethoxybenzaldehyde (Example II) (Birch, A. J., Jackson, A. H., Shannon, P. V. R. and Steward, G. W., Journal of Chemical Society Perkin Trans I, 2492–2501, (1973) and Starkovsky, N. A., Journal of Organic Chemistry, 27, 3733–3734, (1962)) (ii) direct oxidation of β-asarone with selenium dioxide (Liu M C, Lin T S & Sartorelli A C, J Med Chem, 35, 3672 (1992)) into 2,4,5-trimethoxycinnamaldehyde (Example III) and its comparison with reported natural cinnamaldehyde. Treatment of β-asarone with selenium dioxide and few drop of base such as pyridine, triethylamine etc in dioxane gave two distinguished spots on TLC plate in which one yellow spot is expected for 2,4,5-trimethoxycinnamaldehyde while minor spot for corresponding cinnamyl alcohol derivative as clearly confirmed by the absorbance of peak at 1648 (carbonyl) and 3480 (hydroxyl group) in IR spectra. The latter was formed even when the amount of selenium dioxide was increased up to 1.3 equiv. Formation of side product alcohol are common with aldehyde during the allylic oxidation of several analogs of β-asarone with SeO$_2$. However, we observed that without any separation, treatment of the mixture of cinnamaldehyde and cinnamyl alcohol with pyridinium chlorochromate (PCC) (Lin, S. J., Short, R. E., Ford, S. P., Grings, E. E. and Rasazza, P. N., J Nat Prod, 61, 51–56 (1998)) afforded 2,4,5-trimethoxycinnamaldehyde as a single spot since alcohol got oxidized into cinnamaldehyde. The $^1$H-NMR spectral data of cinnamaldehyde is similar to the reported natural (Kulkarni, M. M., Sohani, J., Rojatkar, S. R. and Nagasampagi, B. A., Indian J. Chem., 25B: 981–982 (1986)) and its $^{13}$C-NMR spectral data is reported here for the first time. Thus, isolation and characterization of above cinnamaldehyde has opened a new route to prepare several substituted cinnamaldehydes in a single step starting from phenylpropane derivatives.

After successful assignment of substituted cinnamaldehyde, the applicants main attention was focused on to increase the percentage of cinnamaldehyde (a natural dye) as demand of natural colourants over synthetic ones are increasing worldwide due to their safer and ecofriendly nature. Thus, we observed that treatment of phenylpropane with DDQ ranging from 1 to 20 moles (preferably 1.5 to 8 moles) afford mainly cinnamaldehyde. The formation of unsaturated aldehyde from saturated propane side chain is possible only via initial formation of phenylpropene which further undergo oxidation and lead to the formation of cinnamaldehyde in a single step. The yield of cinnamaldehyde may be further increased by using the catalysts such as mineral acid (hydrochloric acid, sulfuric acid) or Cu(I) or Fe(III) salt or periodic acid or organic acids such as acetic acid, propionic acid, butyric acid, ion exchange resin such as IR-120H, a sulphonated polystyrene resin, para-toluenesulphonic acid (PTSA) etc. The formation of cinnamaldehyde can be carried out in a short time by adsorbing the solution of 1-Propyl-2,4,5-trimethoxybenzene and oxidising reagent DDQ on the following solid support namely celite, silica gel, molecular sieve, alumina under microwave irradiation (Posner, G. H. and Rogers, D. Z. J. Am. Chem. Soc. 99, 8208 (1997); Jr. Filippo, J. S. and Chern, C. I. J. Org. Chem. 42, 2182 (1979) (Example IV) for 40 second to 20 minutes, preferably 2 to 12 minutes. It is worthwhile to mention that among several oxidizing reagents (such as manganese dioxide or p-chloranil or Pyridinium chlorochromate or tBuOOH CrO$_3$), DDQ is found as a powerful dehydrogenating (Sondengam, B. L. and Kimbu, S. F., Tetrahedron Letters, 1: 69–70, (1977) and Guy, A.; Lemaire, M. and Guette, J. P., Chem. Commun. 8 (1980)) and oxidizing reagent (Becker, H. D. J. Org Chem. 30, 982 (1965)) which converts phenylproane derivatives into corresponding cinnamaldehydes as a trans-isomer (Lemaira, M., Guy, A. and Imbert, D., Chem. Commun. 741 (1986) and Ireland, R. E. and Brown, G., Org. synthesis, Coll. Vol. V, 428–431)) in one step. In addition, the DDQ-mediated reactions allow to monitor the progress of the reaction as a green-coloured charge transfer (CT)-complex formed, which gradually changes to pink or brown color (as the 2,3-dichloro-5,6-dicyano-1,4-hydrobenzoquinone crystallized out), indicates the formation of desired products. At the end of the reaction, the precipitated hydrobenzoquinone (DDQH$_2$) can be easily separated by filteration which allow to obtain 2,3-dichloro-5,6-dicyano-1,4-hydrobenzoquinone (DDQH$_2$) in 90 to 94% yield. The amount of precipitated hydroquinone (DDQH$_2$) can be conveniently converted back to DDQ in good yield by standard methods (Walker, D. and Waugh, T. D., J. Org. Chem. 30, 3240, (1965)). In view of all above, the DDQ-mediated conversion of phenylpropane into cinnamaldehyde appears to be industrially attractive method. In addition, hydrogenated crude calamus oil (asarones present from 70 to 96%) can be used directly for oxidation by DDQ for the preparation of 2,4,5-trimethoxycinnamaldehyde is an added benefits since remaining constituents of reduced calamus oil do not interfere during oxidation and the yield was found to be less than just by 5–15% depending upon asarones percentage in calamus oil. Therefore, this invention makes above process further cost effective.

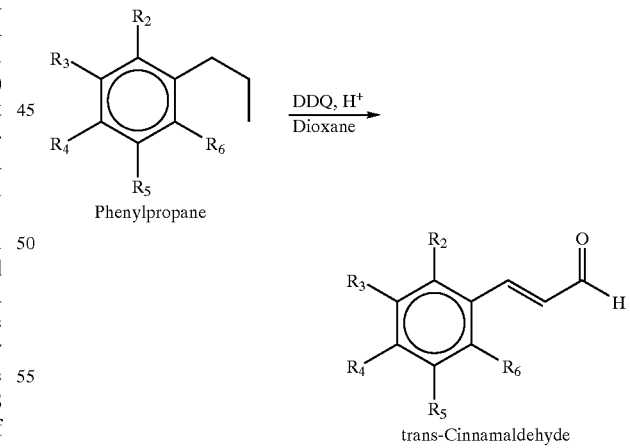

Phenylpropane trans-Cinnamaldehyde

Thus, applicants the present method for the synthesis of substituted cinnamaldehyde is not only simple, cheaper and high yielding but can convert any, kind of substituted phenylpropanes which are even prone to acid or base.

BRIEF DECSRIPTION OF THE ACCOMPANYING DRAWINGS

EXAMPLES

Figure 1:
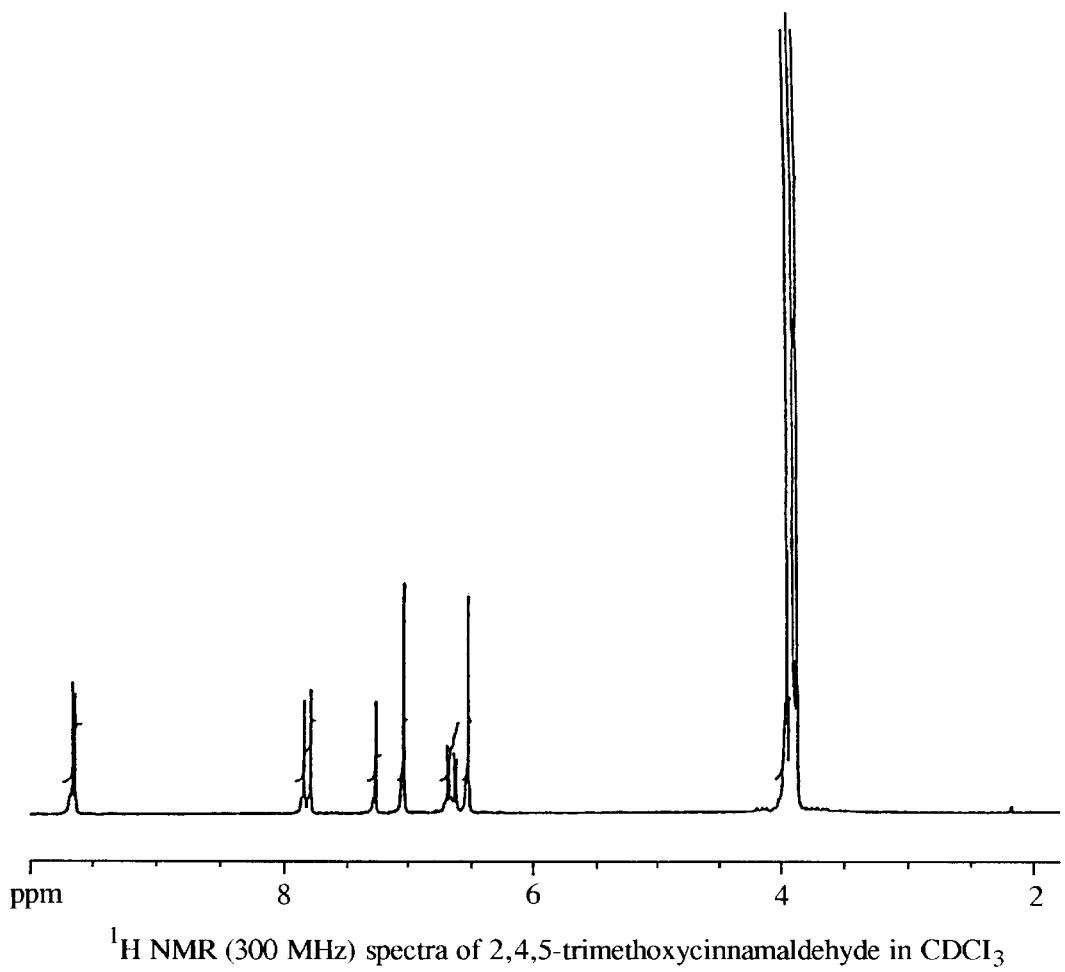
FIG. 1 is $^1$H NMR (300 MHz) spectra 2,4,5-trimethoxycinnamaldehyde (in CDCl$_3$) of the reaction product of Example I containing the compound having the structure ##STR## as shown in FIG. 4.
Figure 2:
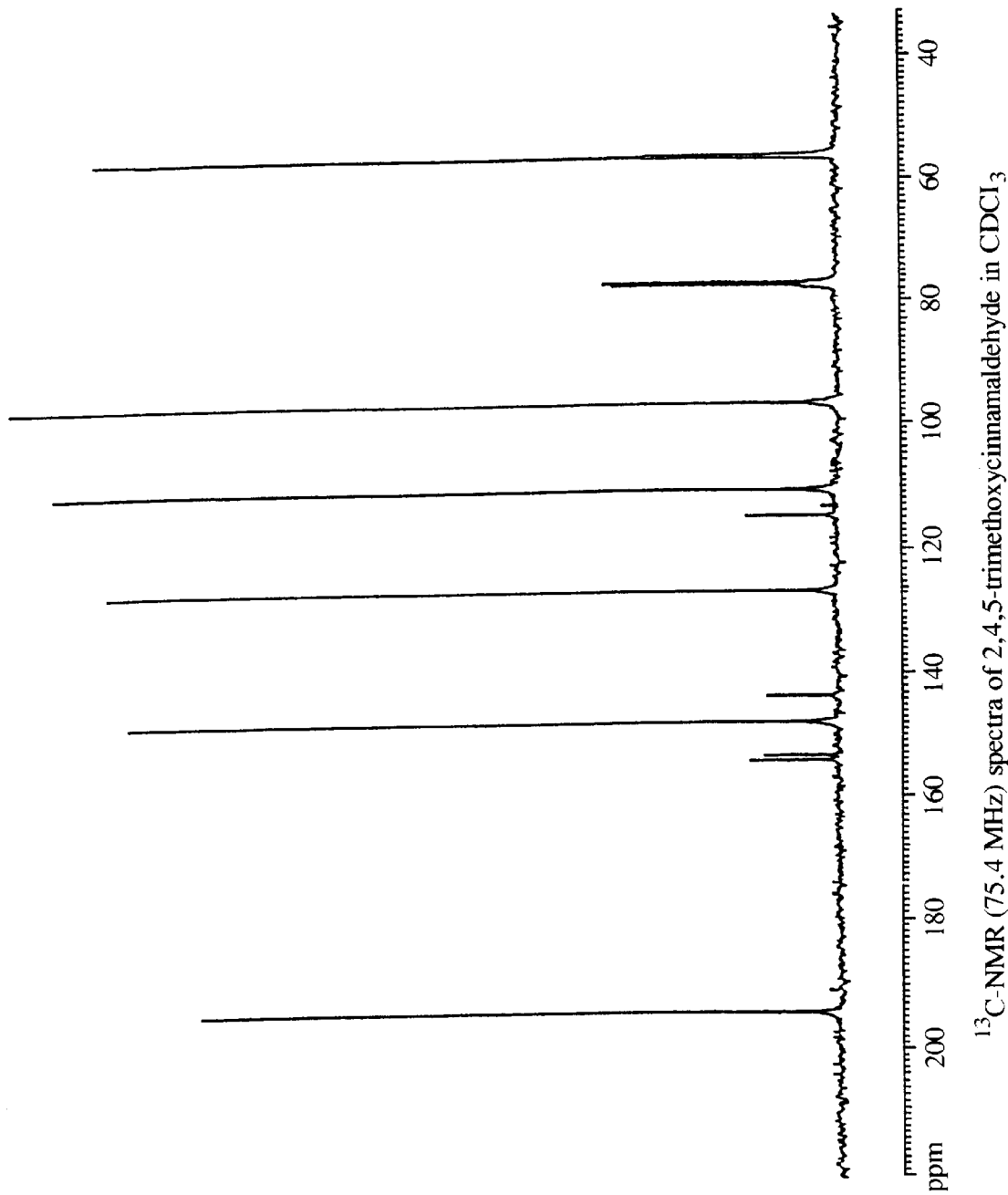
FIG. 2 is $^{13}$C NMR (75.4 MHz) spectra of 2,4,5-trimethoxycinnamaldehyde (in CDCl$_3$) of the reaction product of Example I containing the compound having the structure: ##STR## as shown in FIG. 4.
Figure 3:
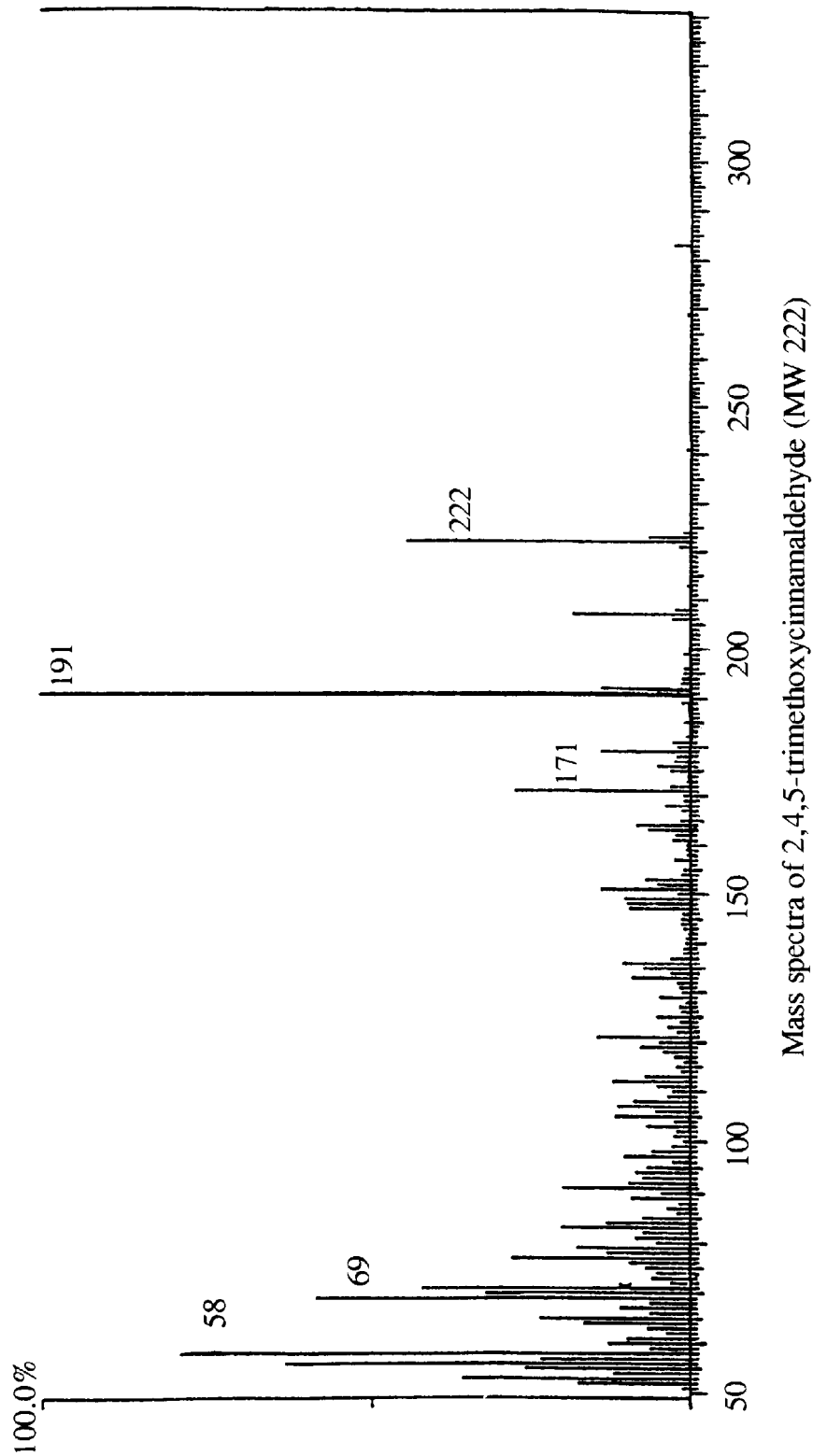
FIG. 3 is the electro spray (ES) mass spectrum of 2,4,5-trimethoxycinnamaldehyde (MW 222) of the reaction product of Example I containing the compound having the structure ##STR## as shown in FIG. 4.
Figure 4:
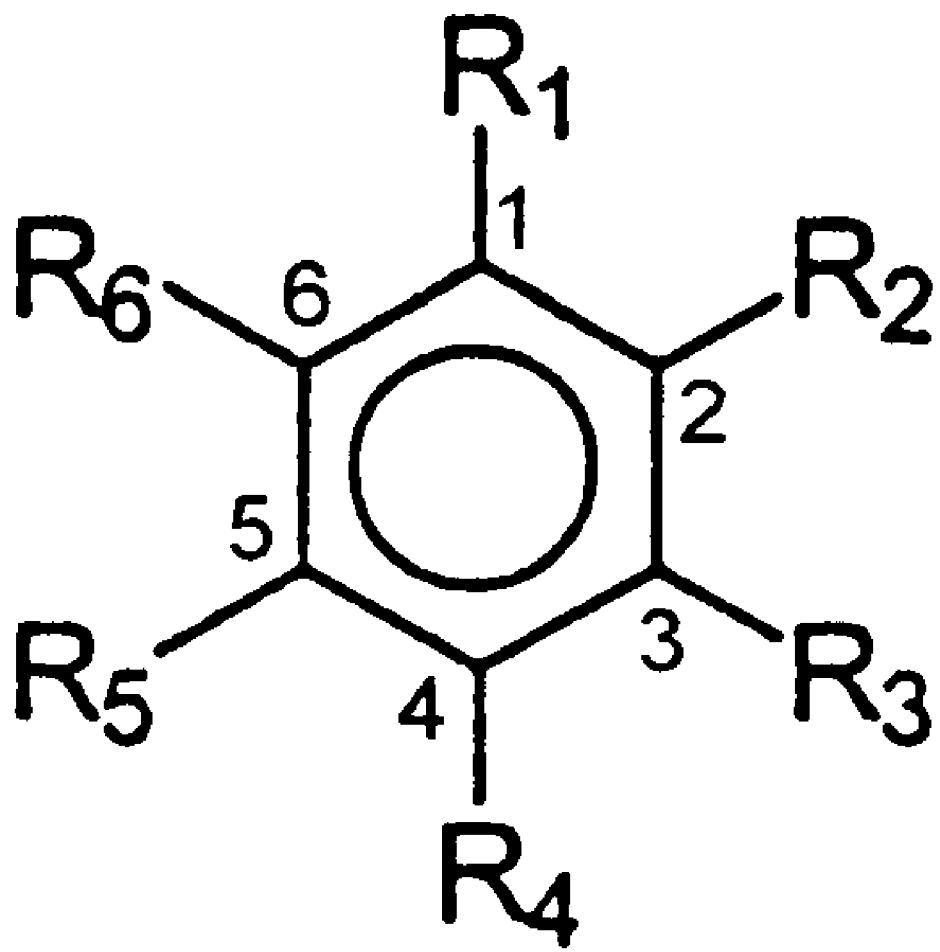
FIG. 4 is the structure of substituted trans-cimmanaldehyde.

The following examples are given by way of illustration of the present invention and should not be construed to limit the scope of the present invention.

The starting material phenylpropane derivatives such as dihydroeugenol (n-Propyl guaiacol), 3,4-Methylenedioxy phenylpropane (dihydrosafrole), 4-Methoxyphenylpropane (dihydroanethole) or the like, can be obtained either from commercial sources or by catalytic hydrogenation of corresponding eugenol, safrole, anethole derivatives respectively (Steffen, A. In: Perfume and Flavor Chemicals, Allured Punlishing Corporation, 362 South Schmale Road, Carol Stream, Ill., USA, (1994)). In addition, 2,4,5-Trimethoxyphenylpropane can be obtained via ammonium formate assisted reduction of toxic β-asarone of Acorus calamus or crude calamus oil containing β-asarone (Sinha, A. K., U.S. Ser. No. 09/652,376 filed on Aug. 31, (2000)).

Example I

Synthesis of 2,4,5-Trimethoxycinnamaldehyde From 2,4,5-Trimethoxyphenylpropane (by Thermal Method)

A solution of 2,4,5-Trimethoxyphenylpropane (5 g) in 70 mL of dry dioxane was placed in 100 ml round bottom flask. To this was added a catalytic amount of acetic acid (2–4 drops) and 16 g of DDQ and finally started refluxing the mixture at 50 to 140° C. for 5 to 9 hrs. The solution, which was initially deep green, turned into pale yellow with the formation of hydroquinone (DDQH$_2$). The mixture was cooled and the solid DDQH$_2$ was filtered and further washed with chloroform. The filtrate and washings were combined and evaporated under reduced pressure. The product was taken in ether (80 ml) and the ether layer was washed with aqueous NaOH (15%, 2×15 ml). The combined aqueous layers are further extracted with ether (3×15 ml). The ether layers were combined and washed with saturated sodium chloride (3×15 ml), dried over anhydrous sodium sulphate and filtered. The solvent was removed to afford a crude yellow liquid which was loaded on silica gel column and the column was eluted with hexane (70–80 ml) and then with an increasing amount of hexane/ethyl acetate (9:1 to 1:9). The fractions were monitored on TLC plate and the desired fractions were combined and solvent was removed under vacuum to afford 2,4,5-trimethoxycinnamaldehyde in 82% yield as a yellow solid; mp 140° C.; UV (MeOH) λmax 244, 298, 366 nm; IR (film) vmax 1648 (conjugated carbonyl), 1602, 1504, 1466, 1448, 1350, 1254, 1120, 1024, 856 cm$^{-1}$; $^1$H NMR δ 9.65 (1H, d, J=7.8 Hz, H-3'), 7.81 (1H, d, J=15.8 Hz, H-1'), 7.03 (1H, s, H-6), 6.64 (1H, dd, J=15.8 Hz, J=7.8 Hz, H-2'), 6.51 (1H, s, H-3), 3.95 (s, 3H, 2-OCH$_3$), 3.91 (s, 3H, 4-OCH$_3$), 3.87 (s, 3H, 5-OCH$_3$); $^{13}$C NMR δ 194.1 (C-3'), 154.1 (C-1'), 153.2 (C-2), 147.6 (C-4), 143.3 (C-5), 126.4 (C-2'), 114.5 (C-1), 110.5 (C-6), 96.5 (C-3), 56.4 (5-OCH$_3$), 56.2 (2-OCH$_3$), 56.0 (4-OCH$_3$); EIMS m/z 222 [M]$^+$ (44), 207 (18), 191 (100), 179 (14), 171 (27), 151 (14), 147 (7), 69 (58), 58 (80).

Example II

Permanganate Oxidation of the 2,4,5-Trimethoxycinnamaldehyde Into 2,4,5-Trimethoxybenzaldehyde A solution of the 2,4,5-Trimethoxycinnamaldehyde (0.5 g) was treated with KMnO$_4$ (0.5 g) in dry acetone (20 ml). The reaction mixture was left at room temperature for 24 hr, manganese dioxide was filtered off and the solvent was removed. The residue was dissolved in ethyl acetate and washed carefully with 10% NaHCO$_3$, brine, and dried over anhydrous Na$_2$SO$_4$. Evaporation of the solvent afforded a crude solid, which was further recrystallised from water to afford 0.2 g 2,4,5-trimethoxybenzaldehyde as a colorless solid, mp 114° C. (lit. mp 114° C.); IR (film) vmax 1662 (carbonyl group), 1620, 1518, 1481, 1419, 1361, 1300, 1278, 1222, 1199, 1138, 1025, 865 cm$^{-1}$; $^1$H NMR δ 10.32 (1H, s, CHO), 7.33 (1H, s, 6H), 6.50 (1H, s, 3H), 3.98 (3H, s, 2-OCH$_3$), 3.93 ((3H, s, 4-OCH$_3$), 3.88 (3H, s, 5-OCH$_3$); $^{13}$C NMR δ 187.96 (CHO), 158.60 (C-2), 155.76 (C-4), 143.56 (C-5), 117.35 (C-1), 109.03 (C-6), 56.19 (2-OCH$_3$, 4-OCH$_3$ and 5-OCH$_3$); EIMS m/z 196 [M]$^+$ (100), 181 (49), 150 (32), 125 (33), 110 (23), 69 (37).

Example III

Synthesis of 2,4,5-Trimethoxycinnamaldehyde From β-Asarone (by Thermal Method)

A mixture of β-asarone (1.87 g), selenium dioxide (0.90 g) and dioxane (30 ml) containing 0.3 ml of water was refluxed for 6 h. Additional selenium dioxide (0.21 g) was added to the mixture, and the mixture was refluxed for further 12 h. The mixture was cooled and filtered to remove the precipitated black selenium. The filtrate was evaporated under reduced pressure and the resulting residue was redissolved in CH$_2$Cl$_2$, washed with brine, and dried over anhydrous Na$_2$SO$_4$. Evaporation of the solvent afforded a mixture of 2,4,5-trimethoxycinnamaldehyde and corresponding alcohol (as formation of side product alcohol is common with aldehyde during the allylic oxidation of several analogs of β-asarone with SeO$_2$) which was directly treated with excess of pyridinium chlorochromate (1 g) in dry CH$_2$Cl$_2$ (50 ml). After being stirred at room temperature for overnight, the reaction mixture was filtered over a short pad of celite. The filtrate was concentrated under reduced pressure and residue was column chromatographed over silica gel (petroleum ether/EtOAc 9:1 to 1:9) to give 52% of 2,4,5-trimethoxycinnamaldehyde as a yellow solid; mp 140° C. TLC, CoTLC, physical and spectral data is exactly the same as above trimethoxycinnamaldehyde (Example I).

Example IV

Oxidation of 4-Methoxy Phenylpropane Into 4-Methoxycinnamaldehyde (by Microwave Irradiation)

A mixture of 4-methoxy phenylpropane (2 g), silica gel (0.5–0.8 g), DDQ (7.5 g) and dioxane (5–8 ml) was taken in a 100 ml Erlenmeyer flask fitted with a loose funnel at the top. The flask was placed inside a microwave oven operating at medium power (600 W) and irradiated for 2–8 minutes.

After completion of the reaction (monitored by TLC), the contents of the flask were poured into chloroform and passed through a bed of Celite and further washed with chloroform. The filtrate and washing were combined and the chloroform layers were washed with an aqueous NaOH (15%, 3×15 ml). The combined aqueous layers were further extracted with chloroform (3×15 ml). The chloroform layers were then combined and washed with saturated sodium chloride (3×15 m), dried over anhydrous sodium sulphate and filtered. The solvent was removed to afford a crude product which was loaded on silica column and the column was first eluted with hexane (70–80 ml) and then with an increasing amount of hexane/ethyl acetate (9:1 to 1:9). The fractions were monitored on TLC plate and the desired fractions were combined and solvent was removed under vacuum to afford 4-methoxy cinnamaldehyde in 68% yield as a solid; mp 57–58° C.; (lit. mp 58° C.). The physical and spectral data was found to similar as reported.

Example V

Synthesis of 3,4-Dimethoxycinnamaldehyde From 3,4-Dimethoxyphenylpropane (by Thermal Method)

A solution of 3,4-dimethoxyphenylpropane (1 g) in 40 mL of dry dioxane was placed in 100 ml round bottom flask. To this was added a catalytic amount of para-toluenesulphonic acid (0.04 to 0.1 g and 4.5 g of DDQ and finally started refluxing the mixture at 50 to 140° C. for 7 to 16 hrs. The mixture was cooled and the precipitated $DDQH_2$ was filtered and further washed with chloroform. The filtrate and washings were combined and evaporated under reduced pressure. The product was taken in ether (50 ml) and the ether layer was washed with aqueous NaOH (15%, 2×10 ml). The combined aqueous layers are further extracted with ether (3×10 ml). The ether layers were combined and washed with saturated sodium chloride (3×10 ml), dried over anhydrous sodium sulphate and filtered. The solvent was removed to afford a crude yellow liquid which was loaded on silica gel column and the column was eluted with hexane (40–50 ml) and then with an increasing amount of hexane/ethyl acetate (9:1 to 1:9). The fractions were monitored on TLC plate and the desired fractions were combined and solvent was removed under vacuum to afford 3,4-dimethoxycinnamaldehyde in 79% yield as a yellow solid; mp 74–77° C. ; $^1$H NMR δ 9.67 (1H, d, H-3'), 7.43 (1H, d, H-1'), 7.15 (1H, d, H-5), 7.08 (1H, s, H-3), 6.91 (1H, d, H-3), 6.61 (1H, dd, H-2'), 3.94 (s, 3H, 3-$OCH_3$), 3.93 (s, 3H, 4-$OCH_3$). The remaining physical and spectral data was found similar as reported.

The Main Advantages of the Present Invention are
1) A simple and economical industrial process to
2) A simple process to convert phenylpropane derivatives into corresponding cinnamaldehyde in high yields.
3) A simple process to convert phenylpropane derivatives into corresponding trans-cinnamaldehyde, since trans-form is preferred isomer and also found frequently in plant kingdom.
4) A process to convert an internationally banned toxic compound β-asarone or calamnus oil or safrole oil or the like into useful products.
5) Introduction of a series of yellow coloured dyes some of which are not available on a commercial scale.
6) Preparation of a natural dye such as 2,4,5-trimethoxycinnamaldehyde as an inexpensive and simple starting material for corresponding acid, ester, alcohol and dihydro alcohol, acid, ester, aldehyde and alkaloid or the like.
7) The present chemical process can increase the price of calamus oil as demand for new natural colouring dyes goes up as presently, calamus oil of tetraploid or hexaploid varieties (distributed extensively in Asian origin) has very low price in comparison to the oil of diploid and triploid (distributed in American or European origin) varieties.
8) A process of converting phenylpropane obtained from readily available and cheaper phenylpropene bearing essential oil.
9) A simple process by which any kind of aromatic compound having propane side chain or the like can be converted into cinnamaldehyde.
10) A simple process for preparation of cinnamaldehyde in which any kind of pressure application or explosive reagents are not required.
11) A simple process for the preparation of cinnamaldehyde, which even completed in few seconds to minutes under microwave irradiation.
12) A simple process for preparation of cinnamaldehyde in which percentage of cinnamaldehyde is further increased by using catalyst such as acetic acid, p-toluene sulphonic acid or silica gel etc.

What is claimed is:

1. A process for the preparation of substituted trans-cinnamaldehyde, a class of natural yellow dye represented by formula (I):

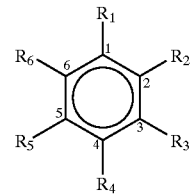

Formula I wherein $R_1$=CH=CH—CHO with at least one hydrogen atom selected from substituents represented by $R_2$, $R_3$, $R_4$, $R_5$ and $R_6$, and a methylenedioxy group formed by the combination of at least two of these adjacent substituents represented by $R_2$, $R_3$, $R_4$, $R_5$ or $R_6$, together with other substituents selected from the group consisting of hydroxyl protected hydroxyl acyl, hydroxyl protected hydroxyl benzyl, alkoxy, alkyl and aryl group, the process comprising steps of:

a) oxidizing substituted phenyl propane derivatives in a solvent in presence of a catalyst and an oxidizing agent at temperature between −15° to +210° C. for a period of 0.5 to 48 hours,
　b) cooling a reaction mixture of step (a) and filtering an unwanted solid and separating a clear mother liquor,
　c) removing a solvent from the clear mother liquor of step (b) under reduced pressure to yield a residue,
　d) providing a solution of the residue of step (c) in an organic solvent, optionally washing with aqueous alkali solution, followed by brine solution and separating an organic layer and discarding an aqueous layer,
　e) drying the organic layer of step (d) over anhydrous sodium sulphate, filtering; and evaporating to the organic layer to obtain a second residue, and
　f) purifying the second residue of step (e) by column chromatography over silica gel to obtain compounds of formula (I) in a yield ranging between 68–72%.

2. A process for the preparation of substituted trans-cinnamaldehyde derivatives comprising oxidizing a substituted phenylpropane in the presence of a solvent, a catalyst and an oxidizing agent with a solid support under micro wave irradiation at a medium power 600 W for a period 20 seconds to 12 minutes, removing the solvent under reduced pressure and obtaining the trans-cinnamaldehyde of formula 1:

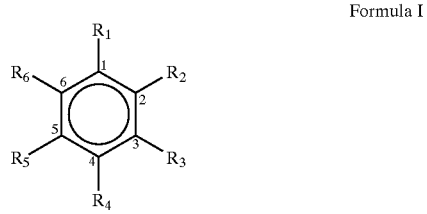

Formula I in a yield ranging between 68% and 72%.

3. A process as claimed in claim 1 wherein, the solvent used is selected from the group consisting of diethyl ether, tetrahydroduran, dimethoxyethane, dioxane, diphenylether, chlorinated solvent selected from the group consisting of dichloromethane, chloroform and o-dichlobenzene, an aromatic hydrocarbon selected from the group consisting of benzene, toluene, xylene and an organic acid selected from the group consisting of formic acid, and acetic acid.

4. A process as claimed in claim 1 wherein, the oxidizing agent used is selected from the group consisting of 2,3-dichloro-5,6-dicyano-1,4-benzoquinone (DPQ), p-chloranil, pyridinium chlorochromate (PCC), t-butylperoxide (tBuOOH) and chromium trioxide ($CrO_3$).

5. A process as claimed in claim 1 wherein, the mole ratio of oxidising agent to reactant ranges from 1:1.5 to 1:5.

6. A process as claimed in claim 1 wherein, the reaction temperature ranges from 30° C. to 140° C.

7. A process as claimed in claim 1 wherein, the reaction period ranges from 4–16 hours.

8. A process as claimed in claim 1 wherein, the catalyst used is selected from the group consisting of hydrochloric acid, sulfuric acid, Cu(I) salt, Fe(III) salt, periodic acid, an organic acid selected from acetic acid, propionic acid and butyric acid, ion exchange resin selected from IR-120H and a sulphonated polystyrene resin and amberlyst.

9. A process as claimed in claim 1 wherein, the starting material phenylpropane used is obtain by reduction of allylbenzene or phenyl propene derivatives or natural allyl and phenyl propene derivatives existing in three isomeric forms.

10. A process as claimed in claim 1 wherein, the oxidation of phenylpropane provides trans-cinnamaldehyde.

11. A process as claimed in claim 1 wherein, a toxic beta(cis)cinnamaldehyde isomer and a γ-cinnamaldehyde isomer are isolated.

12. A process as claimed in claim 1 wherein, an beta-asarone is converted into a yellow dye.

13. A process as claimed in claim 1 wherein, greater than 1 kilogram of trans-cinnainaldehyde derivative is produced.

14. A process as claimed in claim 1 wherein, the cinnamaldehyde derivatives produced are colorants, antioxidant or antimicrobial agents.

15. A process as claimed in claim 1 wherein, the by-product $DDQH_2$ is formed and 91–94% is regenerated into DDQ.

16. A process as claimed in claim 1 or 2 wherein, the process oxidizes phenyl alkane where the alkyl group attached to a phenyl ring is represented by 2n−1 carbon atoms, wherein n is an integer between 2 and 6.

17. A process as claimed in claim 1 wherein, the above phenylpropane derivatives undergo a reaction selected from the group consisting of halogenation, dehydrogenation, allylic halogenation, formylation, monocarbonylation, dicarbonylation and condensation.

18. A process as claimed in claim 1 wherein, the process provides cinnamaldehyde derivatives without any contamination of corresponding acid and alcohol.

19. A process as claimed in claim 1 wherein, a cinnamaldehyde derivative trans-2,4,5-trimethoxycinnamadehyde is obtained and further used as a starting material for the synthesis of unsaturated acids, esters, amides or alcohol derivatives.

20. A process as claimed in claim 1 wherein, a cinnamaldehyde derivative trans-2,4,5-trimethoxycinnamaldehyde is obtained and further used as a starting material for the synthesis of dihydro (saturated) acids, esters, amides or alcohols derivatives.

21. A process as claimed in claim 1 wherein, the products obtained are trans-2,4,5-trimethoxycinnamaldehyde, p-methoxycianamaldehyde and 3,4-dimethoxycinnamaldehyde.

22. A process as claimed in claim 2 wherein, the solid support used is selected from a group consisting of celite, silica gel, molecular sieve and alumina.

23. A process as claimed in claim 2 wherein, the products obtained are trans-2,4,5-trimethoxycinnamaldehyde, p-methoxycinnamaldehyde and 3,4-dimethoxycinnamaldehyde.

* * * * *